United States Patent [19]
Arpentinier et al.

[11] Patent Number: 5,430,181
[45] Date of Patent: Jul. 4, 1995

[54] PROCESS FOR IMPROVING A CONTROLLED OXIDATION REACTION

[75] Inventors: Philippe Arpentinier, Paris; Jacques Koenig, Versailles; Yves Torre, Cressely, all of France

[73] Assignee: L'Air Liquide Societe Anonyme Pour L'Etude et L'Exploitation des Procedes Georges Claude, Paris, France

[21] Appl. No.: 19,878

[22] Filed: Feb. 19, 1993

[30] Foreign Application Priority Data

Feb. 27, 1992 [FR] France ............... 92 02277

[51] Int. Cl.$^6$ ............... C07C 51/10; C07C 51/255;
C07C 37/00; C07C 17/42
[52] U.S. Cl. ............... 562/406; 562/407;
562/412; 562/480; 562/493; 562/590; 562/595;
562/607; 562/887; 568/382; 568/800; 568/801;
568/802; 570/121; 570/243; 549/262; 549/257;
549/258; 549/248
[58] Field of Search ............... 570/116; 568/800, 802,
568/801, 382; 562/406, 407, 412, 480, 493, 590,
595, 607, 887

[56] References Cited

U.S. PATENT DOCUMENTS

| | | | |
|---|---|---|---|
| 4,329,527 | 5/1982 | Kühn et al. | 570/245 |
| 4,849,562 | 7/1989 | Buhs et al. | 570/241 |
| 5,087,779 | 2/1992 | Nubel et al. | 570/245 |

FOREIGN PATENT DOCUMENTS

| | | |
|---|---|---|
| 0029317 | 5/1981 | European Pat. Off. |
| 2281361 | 3/1976 | France |
| 1254137 | 11/1967 | Germany |
| 1462580 | 1/1977 | United Kingdom |

Primary Examiner—C. Warren Ivy
Assistant Examiner—Raymond Covington
Attorney, Agent, or Firm—Oliff & Berridge

[57] ABSTRACT

Process for improving a controlled oxidation reaction between at least one reactant and oxygen, in which at least one reactant is reacted with oxygen or an oxygen containing gas, constituting a reaction mixture, in the presence of at least one additional gas which is introduced into said reaction mixture and is selected from methane, ethane and helium, and the resulting reaction product from the oxidation reaction is possibly treated so as to give a final product.

23 Claims, 2 Drawing Sheets

PROCESS FOR IMPROVING A CONTROLLED OXIDATION REACTION

BACKGROUND OF INVENTION

1. Field of the Invention

The present invention concerns a process for improving the selectivity of a controlled oxidation reaction between at least one reactant and oxygen in order to give a final product for improving either the capacity or the yield of a production unit where this controlled oxidation reaction is carried out.

2. Description of Prior Art

Most of the oxidation reactions which are used in the chemical industry are based on the following scheme:

(I) REACTANT(S)+$O_2\rightarrow$PRODUCT(S) Controlled oxidation (II) REACTANT(S)+$O_2\rightarrow CO_2+H_2O$ Complete oxidation (III) REACTANT(S)+$O_2\rightarrow CO_2+H_2O$ (IV REACTANTS+$O_2\rightarrow$COPRODUCTS Secondary reactions (V) COPRODUCTS+$O_2\rightarrow CO_2+H_2O$ Controlled oxidation reaction (I) is the one leading to the intended product and it is the one that should consequently be preferred as compared to the other reactions.

Reactions (I) and (II) are generally predominant, the others often being clearly less important.

It should be noted that reaction (II) consisting in the total oxidation of the reactants into $CO_2$ and $H_2O$, is clearly more exothermic than main reaction (I).

This type of oxidation reactions, under industrial conditions, usually rely on air as a source of oxygen, the nitrogen from the air being inert towards the reactants used.

The selectivity of the process in terms of intended product is generally low as compared to the maximum theoretical selectivity. This relatively low selectivity is examined by the strong contribution of the secondary reactions, in particular reaction (II), with the corresponding release of heat, which causes technical problems in removing this heat and limits the yield of conversion for each pass.

For a large majority of the processes of oxidation, the selectivity of the intended product and the conversion yield may be improved by increasing the concentration of oxygen in the reaction mixture. This concentration is limited either by technical problems of evacuation of the reaction heat or by the range of inflammability of the mixture at the inlet or the outlet of the reactor as well as at any other point of the reactive section. As a matter of fact, any mixture of combustible reactant and oxygen may ignite when its oxygen content exceeds a certain maximum value, which is inherent to each reaction mixture and to the pressure and temperature conditions used. In the conditions of use of this type of reaction, it is therefore suitable not to exceed this maximum value of oxygen which is permissible at any point of the reactive section of a production unit where the oxidation reaction is used and in particular in the reaction mixture, for example for safety reasons.

It would still be particularly interesting, for a mixture of the same reactant and oxygen, under similar conditions of pressure and temperatures, to improve the removal of the reaction heat and to increase the concentration of oxygen which is permissible in the reaction mixture without for this reason only, of course, igniting it.

German patent 1,254,137 describes a process for the manufacture of ethylene oxide by oxidation of ethylene, in which methane is introduced into the reaction mixture in order to increase the concentration of oxygen in the reaction zone. However, this German patent strictly only concerns the oxidation of ethylene in the presence of methane in order to give ethylene oxide. It is particularly noticeable that ethane is considered within the framework of this oxidation reaction, as having an effect which is contrary to that of methane.

On the other hand, it is indicated in this same German patent that until then, it was considered essential that the concentration of paraffin hydrocarbons in the circuit, and consequently also in the ethylene feed, be reduced to a minimum.

This enables to explain why, since 1962, no other oxidation reaction, except the one described in said German patent, was used in the presence of methane or another paraffin hydrocarbon.

As a matter of fact, if it can be considered that within the framework of the oxidation of alkene, essentially ethylene, in order to give an alkene oxide such as ethylene oxide, methane, contrary to ethane, enables to increase the permissible concentration of oxygen, one skilled in the art would have no reason, in view of said German patent, to use a paraffin hydrocarbon, known to be detrimental in view of its tendency to ignite, in order to increase the concentration of oxygen in another oxidation reaction. In other words, it appears, according to the teaching of this German patent, that the use of methane in order to increase the permissible concentration of oxygen is recommended only in the case of the oxidation of an alkene, such as ethylene, in order to give an alkene oxide, such as ethylene oxide.

The German patent has not solved one of the problems raised above, namely, increasing the concentration of permissible oxygen in a reaction mixture in order to increase the productivity of any controlled oxidation reaction other than the oxidation of an alkene to give an alkene oxide.

The present invention therefore concerns a process enabling to improve the selectivity of a controlled oxidation reaction. A second object of the invention consists in enabling to increase the concentration of permissible oxygen in the reaction mixture and this, without any problem of safety.

A third object of the invention consists in providing a reaction mixture in which the thermic properties for example heat conductivity and specific heat, are improved, thereby permitting a better control of the temperature of the oxidation reaction, as well as an easier removal of the reaction heat at the level of the reactor.

Another object of the invention consists in improving the capacity or yield of a production unit in the operation of a controlled oxidation reaction.

SUMMARY OF INVENTION

The present invention therefore concerns a process for improving a controlled oxidation reaction between at least one reactant and oxygen or a gas containing oxygen, which constitute a reaction mixture, characterized in that at least one reactant is reacted with oxygen in the presence of at least an additional gas which is introduced in said reaction mixture and is selected from methane, ethane, and helium, and, possibly, the product resulting from the oxidation reaction is treated in order to give a final product, the oxidation reaction of an alkene by means of oxygen in order to give an alkene oxide being excluded.

BRIEF DESCRIPTION OF DRAWINGS

Other characteristics and advantages of the present invention will now be described with reference to the annexed drawings in which.

DESCRIPTION OF PREFERRED EMBODIMENT

Usually, the molar content of the additional gas which is introduced into the reaction mixture, which consists of the reactant(s) and oxygen used, is between 5 and 80%, preferably between 10 and 70% and more generally between 20 and 60%.

The oxygen used in the controlled oxidation reaction, according to the process of the invention, may be pure oxygen or a gas containing oxygen and a gas which is inert towards said controlled oxidation reaction.

Such a gas containing oxygen is more often air or oxygen enriched air. It will then be understood that in addition to the additional gas according to the invention, the reaction mixture may include one or more inert gases such as nitrogen.

According to the present invention, the expression "an additional gas introduced into the reaction mixture" means that said additional gas is effectively introduced into the constituted reaction mixture, and also that the additional gas may be previously mixed with oxygen or with the oxygen containing gas, or, preferably with the reactant(s), which will form the reaction mixture.

The additional gas may also result from a controlled oxidation reaction previously used according to the process of the invention, and which is recycled for a new operation, possibly after treatment and/or separation, by adsorption and/or absorption, and/or distillation, and/or fractionated condensation and/or permeation. The unexpected aspect that constitutes the use of such gases is mentioned again here, particularly, methane or ethane as additional inert gas for a controlled oxidation reaction, these gases being normally well known for their property to ignite. This is also more surprising because, within the scope of the present invention, methane and, in a lesser extent ethane, are preferred additional gases for increasing the concentration of oxygen in the reaction mixture, and this still more importantly than helium or carbon dioxide which are reputed to be inert.

It is one of the merits of the present invention to have relied on such properties of these gases in other controlled oxidation reactions than those of the oxidation of an alkene with oxygen of methane to give an alkene oxide, since this type of reaction, up to now, has been considered as a specific case which could not be adapted to other controlled oxidation reactions.

Figure 1:
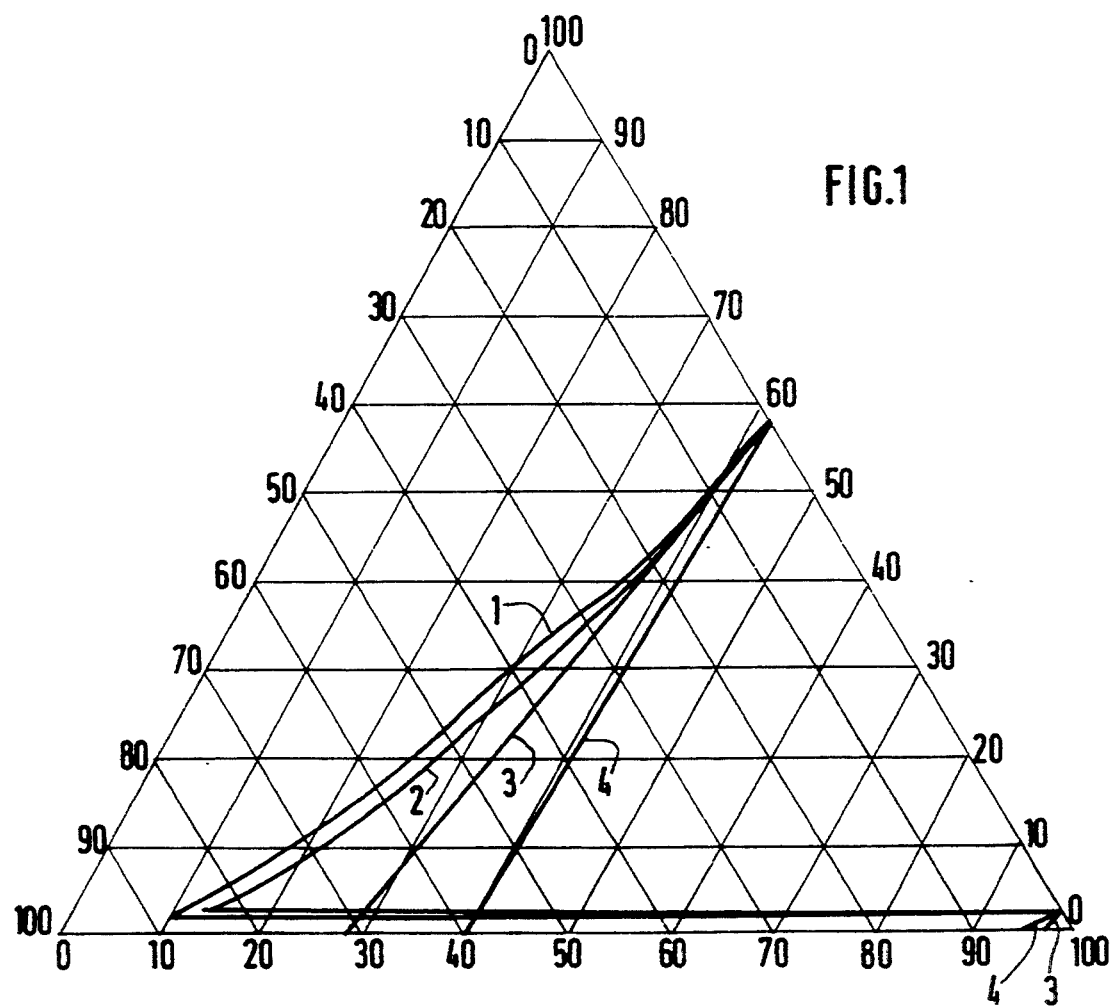
FIG. 1 represents the ternary diagram of the reaction mixture used in the process of oxidizing propylene in order to give acrylic acid in the presence of different additional gases or nitrogen.
Figure 2:
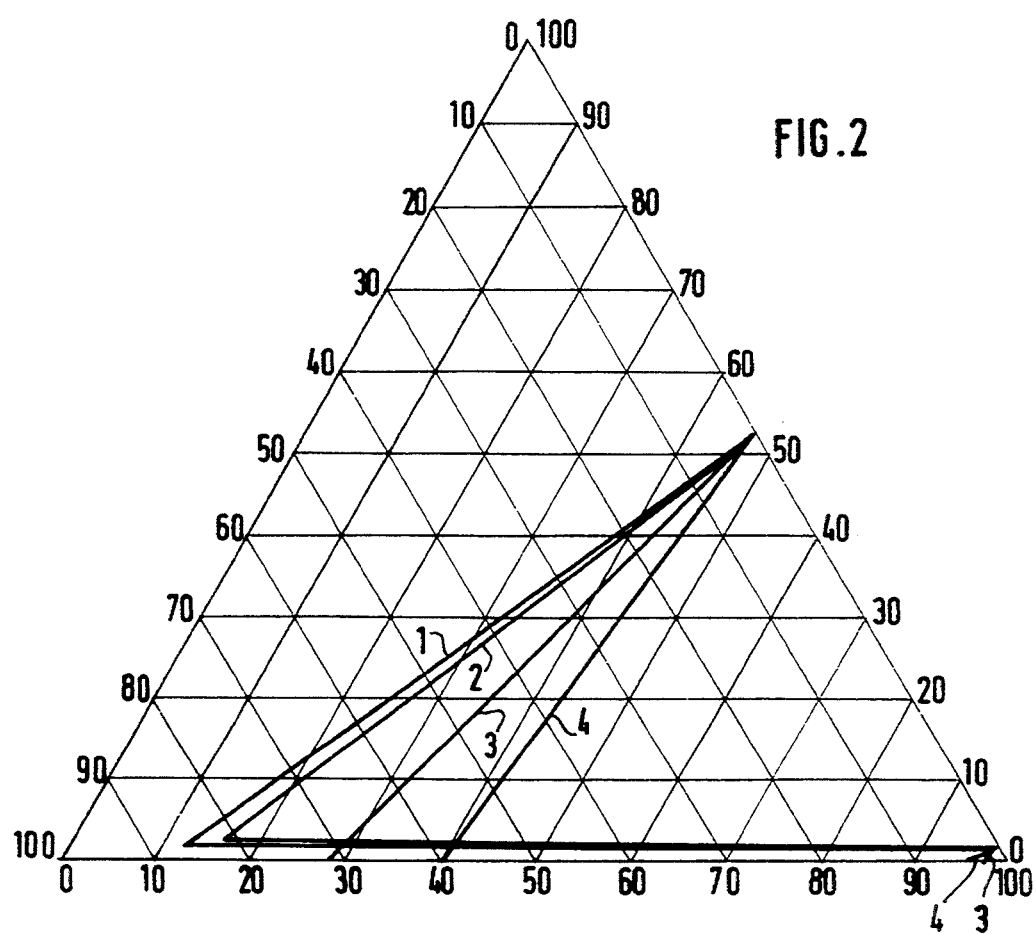
FIG. 2 represents the ternary diagram of the reaction mixture used in the process of oxidizing n-butane in order to give maleic anhydride in the presence of different additional gases or nitrogen.

This possibility of improving controlled oxidation reactions by utilizing an additional inert gas has been proposed as a result of experimental data, on the basis of which ternary diagrams of controlled oxidation reactions which were carried out in the presence of different additional gases and under conditions of pressure and temperature normally used for this type of reaction, have been plotted. It could thus be observed that notwithstanding the nature of the controlled oxidation reaction, the permissible content of oxygen in the reaction mixture is always increased when an additional gas selected from methane, ethane, helium or carbon dioxide is used as compared to another gas, normally nitrogen. FIGS. 1 and 2 show these results in the frame work respectively, of the oxidation of propylene in order to produce acrylic acid and the oxidation of n-butane in order to produce maleic anhydride, carried out under normal conditions of temperatures and pressure. For each of these figures, curves 1, 2, 3 and 4 correspond, respectively, to the use of nitrogen, carbon dioxide, ethane and methane as additional gases.

The plots of these curves have been obtained experimentally according to the method known per se described hereinafter.

In a stainless steel container, provided with an igniting device, predetermined contents of the reactant(s) and of the additional gas have been introduced. These compounds were homogenized by means of a stirring device.

Increasing contents of oxygen are then introduced into the container until the reaction mixture explodes. The oxygen content at which the explosion takes place is indicated on a diagram, as a function of the content of the reactant used.

The operation is repeated many times with variable contents of reactant, so as to permit a plurality of points to be obtained on the ternary diagram.

Depending on the nature of the oxidation reaction, the process according to the invention enables to use a permissible content of oxygen in the reaction mixture which be higher by 1 to 40% molar, more generally 1 to 20% molar (% absolute in the reaction mixture), than the permissible oxygen content when an additional gas according to the invention is not introduced into said reaction mixture.

The oxidation reactions according to the process of the invention may be carried out under atmospheric pressure, but also at a pressure higher than 0.1 MPa, preferably at a pressure between 0.2 and 5 MPa, more preferably between 0.2 and 1.5 MPa.

In addition to their interest in increasing the concentration of permissible oxygen in the reaction mixture which is utilized, the additional gases according to the invention, may also, through their heat conductivity and their specific heat be used to improve greatly the heat conductivity and the global specific heat of the reaction mixture, which facilitates the removal of heat for the same quantity of product being treated.

To the extend that the heat removal from the reaction mixture is improved, it is then possible to increase either the capacity or the yield of a production unit which is used in carrying out a controlled oxidation reaction. Another object of the invention then consists in utilizing at least one additional gas selected from methane, ethane, carbon dioxide and helium in order to improve the removal of reaction heat produced during a controlled oxidation reaction, the oxidation reaction of an alkene by means of oxygen in order to give an alkene oxide being excluded.

In order to carry out the process according to the invention, more particularly for improving the heat conductivity and the global specific heat of the reaction mixture, the additional gas is preferably helium or methane.

The use of an additional gas according to the invention, for example in order to improve the removal of reaction heat, is more particularly adapted to oxidation reactions carried out on a fixed bed.

The process according to the invention may be used to improve any controlled oxidation reaction, whether it be carried out in a gas phase or in a gas-liquid phase.

The process according to the invention in particularly adapted to the following controlled oxidation reactions:
  oxidation of cumene to prepare phenol;
  oxychlorination of ethylene into dichloroethane;
  oxychlorination of benzene to prepare phenol;
  oxidation of toluene to prepare benzoic acid or phenol;
  oxidation of isobutane or ethylbenzene to give propylene oxide;
  oxidation of ethylene in liqud phase to give acetaldehyde;
  oxidation of acetaldehyde, n-butane, light oils (mostly in $C_5$–$C_6$) or n-butenes to give acidic acid;
  oxidation of propylene or isopropanol to give acetone;
  oxidation of ethylene in the presence of acetic acid to give vinyl acetate;
  oxidation of butadiene inithe presence of acetic acid to give butanediol-1,4;
  oxidation of propylene to give acrylic acid;
  oxidation of tertiary butyl alcohol in order to give methacrylic acid;
  oxidation of cyclohexane to give caprolactam and adipic acid;
  oxidation of p-xylene, toluene or p-toluene aldehyde to give terephthalic acid;
  oxidation of p-xylene to give dimethyl terephthalate;
  oxidation of benzene, n-butenes or n-butane to give maleic anhydride;
  oxidation of orthoxylene or naphthalene to give phthalic anhydride;
  oxidation of methanol to give formaldehyde;
  oxidation of glyoxal to give glycol; oxidation of an aldehyde to give carboxylic anhydrides or acids.

The following examples intend to illustrate the invention:

EXAMPLE 1

In order to determine the maximum permissible content of oxygen in a mixture consisting of propylene and oxygen, and used on an industrial basis to produce acrylic acid, the following procedure is followed:

Variable contents of propylene and additional gases or nitrogen are introduced into a stainless steel container which is provided with an igniting device. The mixtures thus obtained are homogenized and increasing contents of oxygen are introduced therein until the mixture ignites.

The conditions of pressure and temperature are those normally used in the industry to carry out this controlled oxidation reaction.

The maximum permissible content of oxygen, beyond which the mixture ignites is given in Table I which follows.

| Propylene (% mol.) | Oxygen (% mol.) | Additional gas or nitrogen (% mol.) | Nature of additional gas |
|---|---|---|---|
| 6.8 | 15 | 78.2 | nitrogen |
| 15.5 | 22 | 62.5 | |
| 6.6 | 18 | 75.4 | $CO_2$ |
| 15.3 | 24 | 60.7 | |
| 8 | 40.3 | 51.7 | methane |
| 28 | 41 | 31 | |
| 4 | 29 | 67 | ethane |
| 13.6 | 32 | 54.4 | |

From Table I, it clearly appears clearly that the oxygen content in the mixture is substantially increased when an additional gas according to the invention is introduced as compared to the permissible oxygen content when only nitrogen is introduced into the mixture.

EXAMPLE 2

The procedure of Example I is repeated in order to determine the maximum permissible oxygen content in a mixture consisting of n-butane and oxygen, which is used on an industrial basis to produce maleic anhydride.

The conditions of pressure and temperature are those normally used in the industry to carry out this controlled oxidation reaction.

The maximum permissible oxygen content beyond which the mixture ignites is given in Table II which follows:

| n-butane (% mol.) | oxygen (% mol.) | additional gas or nitrogen (% mol.) | nature of additional gas |
|---|---|---|---|
| 2.15 | 13 | 84.85 | nitrogen |
| 4.3 | 14 | 82.70 | |
| 8.3 | 17 | 74.70 | |
| 4.15 | 17 | 78.85 | $CO_2$ |
| 8.1 | 19 | 72.90 | |
| 5 | 41 | 54 | methane |
| 10 | 41.8 | 48.20 | |
| 5 | 30 | 75 | ethane |
| 10 | 32 | 58 | |

These results as well as those obtained in Example I, show that the introduction of methane, ethane or carbon dioxide in a mixture enables to substantially increase the maximum permissible content of oxygen.

EXAMPLE 3

Oxychlorination of ethylene in air in a fixed bed.

This reaction is carried out in three reactors disposed in series and operating in a fixed bed. Each reactor includes as catalyst, copper and potassium chlorides supported on balls of alumina of 3 mm diameter.

The first reactor is supplied with the following compounds:

| | % mol. |
|---|---|
| nitrogen | 30 |
| oxygen | 8.8 |
| ethylene | 21 |
| hydrochloric acid | 36.9 |
| helium | 3.3 |

The oxygen introduced into the first reactor represents 80% of the total oxygen used in the process.

The oxychlorination reaction is carried out in each of three reactors at an average temperature of 214° C. and at a pressure of 6.25 bar absolute.

The product mixture resulting from the reaction of oxychlorination from the first reactor is sent into the second reactor, which is supplied with 12% of the total oxygen used, then in the third reactor supplied by the remaining 8% of the oxygen used.

At the outlet of the third reactor, a flow of 443 kilomoles/h of dichloroethane is recovered.

By way of comparison, an oxychlorination reaction is carried out under the same conditions as above, but where helium has been replaced with nitrogen. At the outlet of the third reactor, a flow of 432 kilomoles/h dichloroethane is recovered.

It is therefore observed that the use of helium enables to increase the treatment capacity of the unit by 2.5% which is substantial on an industrial basis. This increase is due to the fact that helium permits a better heat removal from the reaction mixture. Thus, a 30° C. decrease of the temperature of the hot zone was noted in the first reactor when helium was used instead of nitrogen.

We claim:

1. Process for improving by increasing the permissible oxygen concentration in a controlled oxidation reaction between at least one reactant and oxygen, wherein at least one reactant is reacted with at least one member of the group consisting of oxygen and oxygen containing gases, to produce a reaction mixture, in the presence of at least one additional gas different from said at least one reactant which is introduced into said reaction mixture wherein said additional gas comprises at least one member selected from the group consisting of methane and ethane, and wherein the mole content of said additional gas in said reaction mixture is between 3.3 and 80% the oxidation reaction of an alkene by means of oxygen to give an alkene oxide being excluded.

2. Process according to claim 1, wherein the mole content of the additional gas in the reaction mixture is between 5 and 80%.

3. Process according to claim 1, wherein the oxidation is carried out at a pressure which is at least 0.1 MPa.

4. Process according to claim 1, wherein the additional gas is methane or a mixture of methane and any one of ethane, carbon dioxide and helium or a mixture thereof.

5. Process according to claim 1, wherein the permissible content of oxygen in the reaction mixture is higher by 1 to 40% molar, (% absolute in the reaction mixture), than the permissible oxygen content in a same reaction mixture in which no said additional gas has been introduced.

6. Process according to claim 1, wherein the additional gas is pre-mixed with said oxygen.

7. Process according to claim 1, wherein the additional gas introduced into the reaction mixture is obtained from a controlled oxidation reaction carried out according to the process of claim 1.

8. Process according to claim 7, wherein the reaction is carried out after said additional gas is subjected to a separation operation.

9. Process according to claim 1, wherein the controlled oxidation reaction is selected from the group consisting of:

oxidation of cumene to prepare phenol;
oxychlorination of ethylene into dichloroethane;
oxychlorination of benzene to prepare phenol;
oxidation of toluene to prepare benzoic acid;
oxidation of toluene to prepare phenol;
oxidation of isobutane or ethylbenzene to give propylene oxide;
oxidation of ethylene in liquid phase to give acetaldehyde;
oxidation of acetaldehyde to give acetic acid;
oxidation of n-butane to give acetic acid;
oxidation of light oils to give acetic acid;
oxidation of n-butenes to give acetic acid;
oxidation of propylene to give acetone;
oxidation of isopropanol to give acetone;
oxidation of ethylene in the presence of acetic acid to give vinyl acetate;
oxidation of butadiene in the presence of acetic acid to give butanediol-1,4;
oxidation of propylene to give acrylic acid;
oxidation of tertiary butyl alcohol to give methacrylic acid;
oxidation of cyclohexane to give caprolactam and adipic acid;
oxidation of p-xylene to give terephthalic acid;
oxidation of toluene to give terephthalic acid;
oxidation of p-toluene aldehyde to give terephthalic acid;
oxidation of p-xylene to give dimethyl terephthalate;
oxidation of benzene to give maleic anhydride;
oxidation of n-butenes to give maleic anhydride;
oxidation of n-butane to give maleic anhydride;
oxidation of orthoxylene to give phthalic anhydride;
oxidation of naphthalene to give phthalic anhydride;
oxidation of methanol to give formaldehyde;
oxidation of glyoxal to give glycol;
oxidation of an aldehyde to give carboxylic anhydrides; and
oxidation of an aldehyde to give carboxylic acids.

10. Method which comprises using at least one additional gas selected from the group consisting of methane, ethane and carbon dioxide to increase the permissible oxygen content in a controlled oxidation reaction, wherein said oxygen content in said reaction is 1 to 40 mole % greater than the permissible oxygen content in a reaction not containing said additional gas, wherein the mole content of the additional gas in the reaction mixture is between 3.3 and 80% and wherein said at least one additional gas is different from a reactant gas, the oxidation reaction of an alkene by means of oxygen to give an alkene oxide being excluded.

11. Method according to claim 10, wherein said additional gas is methane.

12. Process according to claim 1, wherein a product resulting from the oxidation reaction is treated to give a final product.

13. Process according to claim 1, wherein the molar content of the additional gas in the reaction mixture is between 10 and 70%.

14. Process according to claim 1, wherein the molar content of the additional gas in the reaction mixture is between 20 and 60%.

15. Process according to claim 1, wherein the oxidation is carried out at a pressure which is between 0.2 and 5 Mpa.

16. Process according to claim 1, wherein the oxidation is carried out at a pressure which is between 0.2 and 1.5 Mpa.

17. Process according to claim 1, wherein the content of oxygen in the reaction mixture is higher by 1 to 20% molar (% absolute in the reaction mixture) than the oxygen content in a same reaction mixture in which no said additional gas has been introduced.

18. Process according to claim 1, wherein the additional gas is pre-mixed with said oxygen containing gas.

19. Process according to claim 1, wherein the additional gas is pre-mixed with said at least one reactant.

20. Process according to claim 8, wherein said separation operation is at least one member selected from the group consisting of adsorption, absorption, distillation, fractionated condensation and permeation.

21. Method according to claim 10, wherein said additional gas is a mixture of methane and any one of ethane, carbon dioxide and helium.

22. Process according to claim 1, wherein the additional gas is ethane or a mixture of ethane and any one of methane, carbon dioxide and helium or a mixture thereof.

23. Method according to claim 10, wherein said additional gas is ethane or a mixture of ethane and any one of methane, carbon dioxide and helium or a mixture thereof.

* * * * *